United States Patent [19]
Raleigh et al.

[11] Patent Number: 5,292,503
[45] Date of Patent: Mar. 8, 1994

[54] STABLE WATER IN OIL EMULSIONS

[75] Inventors: William J. Raleigh, Rensselaer; Raymond J. Thimineur, Scotia, both of N.Y.

[73] Assignee: General Electric Company, Waterford, N.Y.

[21] Appl. No.: 773,838

[22] Filed: Oct. 9, 1991

[51] Int. Cl.$^5$ .......................... A61K 7/42; A61K 7/44; A61K 7/48; A61K 9/10
[52] U.S. Cl. ........................... 424/59; 252/309; 424/DIG. 10; 424/DIG. 13; 424/60; 424/65; 514/844; 514/846; 514/847; 514/873; 514/937; 514/941
[58] Field of Search ...................... 424/60, 59

[56] References Cited

U.S. PATENT DOCUMENTS

| | | | |
|---|---|---|---|
| 3,836,647 | 9/1974 | Lange | 424/60 |
| 4,218,250 | 8/1980 | Kasprzak | 106/3 |
| 4,265,878 | 5/1981 | Keil | 424/68 |
| 4,268,499 | 5/1981 | Keil | 424/68 |
| 4,311,695 | 1/1982 | Starch | 424/184 |
| 4,421,656 | 12/1983 | Donatelli et al. | 252/8.5 |
| 4,980,156 | 12/1990 | Raleigh et al. | 424/66 |
| 4,988,504 | 1/1991 | Zotto et al. | 424/65 |
| 5,008,103 | 4/1991 | Raleigh et al. | 424/66 |

OTHER PUBLICATIONS

Hollenberg et al, Chem. Abs., 1988, vol. 110 (22), 198930 Abstract of Euro Pat 271,925.
Nicoll et al, Chem. Abs., 1991, vol. 116 (8), 66929e, Abstract of Euro Pat 456,459.
Iwatani et al, Chem. Abs., 1987, vol. 107 (18), 161409h, Abstract of Japanese Patent No. 62145011.

*Primary Examiner*—Dale R. Ore

[57] ABSTRACT

There is described water-in-oil emulsions containing polysiloxane surface active agents which can be formulated into lotions for use in sunscreens and skin care products.

6 Claims, No Drawings

STABLE WATER IN OIL EMULSIONS

FIELD OF THE INVENTION

The present invention relates to water-in-oil emulsions containing surface active agents of polysiloxane. More particularly, the present invention relates to sunscreens and skin care lotions containing water-in-oil emulsions containing polysiloxane surface active agents having radial organic polyether groups.

BACKGROUND OF THE INVENTION

The use of polysiloxane surface active agents containing radial organic polyether groups to stabilize silicone emulsions is well known. U.S. Pat. No. 4,265,878 uses a polysiloxane surface active agent to stabilize antiperspirant stick compositions. U.S. Pat. No. 4,218,250 uses such a polysiloxane surface active agent to stabilize polish formulations. U.S. Pat. No. 4,268,499 uses these surface active agents to stabilize antiperspirant emulsion compositions. Further, U.S. Pat. No. 4,311,695 uses such surface active agents in personal care creams and the like.

Also, mention is made of U.S. Pat. No. 4,980,156, which describes improved antiperspirant compositions comprising an emulsion of an aqueous astringent in a volatile silicone fluid. Further, special mention is made of U.S. Pat. No. 4,988,506, which describes polysiloxane surface active agents having high molecular weight.

The subject polysiloxane surface active agents are generically known and are sometimes referred to as siloxaneoxyalkylene copolymers. However, their use to date has been directed to stabilizing silicone emulsions in skin care creams and antiperspirant sticks. However, their use in forming stable lotions has not been completely satisfactory, due to emulsion instability, because the variables affecting their function are not well understood. As will be shown in the appended examples, if, instead of antiperspirant sticks, lotions are made using a lipophilic organic surfactant together with a lipophilic polysiloxane copolymer (e.g., U.S. Pat. No. 4,988,504) they show low emulsion stability and relatively low freeze/thaw resistance. Surprisingly, however, it has now been found that if a hydrophilic surfactant is used together with certain lipophilic polysiloxane copolymers, in lotions, long term stable emulsions with excellent resistance to freeze/thaw cycling are obtained.

It is the object of the present invention to produce novel skin care and sunscreen lotions having superior emulsion stability containing surface active agents comprising an organic hydrophobic surfactant and a siloxane surfactant containing radial organic polyether groups.

It is another object of the present invention to provide a water-in-oil silicone emulsion having excellent freeze-thaw stability.

SUMMARY OF THE INVENTION

Briefly, there is provided by the present invention an improved water-in-oil emulsion sunscreen or skin care lotion comprising (a) from 89.5 to about 40 parts by weight of an aqueous solution as a discontinuous phase; (b) from about 10 to about 45 parts by weight of a volatile liquid having a normal boiling point of less than 250° C. as a continuous phase, the volatile liquid being selected from the group of organosiloxane fluids having the average unit formula $(CH_3)_aSiO_{(4-a)/2}$, wherein "a" has an average value of from 2 to 3, inclusive; (c) from about 0.1 to about 3 parts by weight of an organic oil-in-water type surfactant having an HLB value of from 8 to 18, inclusive; and (d) from about 0.4 to about 20 parts by weight of a polyorganosiloxane polyoxyalkylene copolymer surface active agent of the formula $MD_xD'_yM$, wherein D is $R_2SiO_{2/2}$ where R is hydrogen or a substituted or unsubstituted hydrocarbon radical of from 1 to about 12 carbon atoms, D' is $RR'SiO_{2/2}$ where R is as defined above and R' is a polyalkylene ether of the formula $-R^3_a-(OR^2)_n-OR^4$ where $R^2$ is a $-CH_2-CH_2-$ group, $R^3$ is a substituted or unsubstituted alkylene group of 1 to 20 carbon atoms, $R^4$ is the same as R, n has a value of from 5 to about 20, and a is 0 or 1; M represents trimethylsiloxy endcapping units, x is from about 335 to about 475, and y is from about 4 to about 23; with the proviso that the molecular weight of polysiloxane units D is from about 25,000 to about 35,000 and the weight ratio of D to D' is from greater than 60/40 to 90/10.

The emulsions of the present invention are in the form of a lotion and preferably comprise an additive (e) selected from the group consisting of an antiperspirant, a humectant, an insect repellent, an odorant, a deodorant, an emollient, an antiseptic, a sunscreen agent, a cleansing agent, a suitable pharmaceutical, a pigment, a biocide, and mixtures of any of the foregoing. Most preferred are sunscreen agents such as titanium dioxide, UVA and UVB filters which are known to those skilled in the art and are available commercially.

Typically, the UV filters are selected from para amino benzoic acid (PABA) and para amino benzoates, salicylates, cinnamates, benzophenones, anthranilates, dibenzoyl methanes, camphor derivatives and mixtures thereof.

Suitable R groups include hydrogen, methyl, ethyl, vinyl, phenyl, trifluoropropyl, etc. Preferably, at least 80% by number of all R groups are methyl.

$R^2$ may be $-CH_2-CH_2-$, $-CH_2CH(CH_3)-$, $-CH_2C(CH_3)_2-$, $-CH_2CH_2CH_2CH_2-$, etc. However, it is preferred that at least 50% by number of $R^2$ units are $-CH_2CH_2-$.

It is preferred herein that the number of repeating units of R', i.e. the value of n, be between about 5 and 20. Thus, in the case of ethylene oxide as the repeating unit, the molecular weight of R' should be less than about 900. The preferred value of n is from 10 to 15, which likewise for ethylene oxide provides a molecular weight of R' of no more than about 700.

$R^3$ is the group which bonds the polyoxyalkylene segment to the polysiloxane. Preferably, this group is derived from alpha-beta unsaturated carboxylic acids or alcohols. Thus, $R^3$ may be $-CH_2CH_2CH_2-$, $-CH_2CH_2-$, $-CH_2CH_2CH_2CH_2-$, $-(CH_2)_{10}(C=O)-$ etc. Preferably, $R^3$ is $-CH_2CH_2CH_2-$. Otherwise, "a" could be 0 and the segments joined by $-O-$, which is the product of a condensation reaction between a condensable substituent on the polysiloxane and a condensable end group on polyalkylene oxide.

$R^4$ is the terminal group of the polyalkylene ether. The type of $R^4$ is not critical and may be selected from hydrogen, methyl, ethyl, propyl, butyl, phenyl, alkenyl, acetyl, etc. Preferably, $R^4$ is hydrogen.

The polysiloxane absent R' should have a molecular weight between about 15,000 about 50,000 and preferably between 25,000 and 35,000.

DETAILED DESCRIPTION OF THE INVENTION

Component (a) of the present invention is the discontinuous phase. The discontinuous phase preferably comprises water.

However, it is also contemplated that the discontinuous phase can comprise liquid media other than water. Suitable liquid media are organic compounds such as alcohols, including methanol, ethanol, phenol, ethylene glycol, propylene glycol, glycerine, their partial ethers and partial esters; nitrogen compounds including amides such as formamide, acetamide, N,N-dimethyl formamide and urea; nitriles such as acetonitrile, and amines and their salts; acids such as formic acid, acetic acid, benzoic acid, stearic acid and ethylene diaminetetraacetic acid; and ethers such as furan, tetrahydrofuran, dioxane, ethylene glycol dimethyl ether, propylene glycol dimethyl ether and their polymeric forms such as triethylene glycol diethyl ether. Mixtures of any of the foregoing and mixtures of any of them with water are contemplated by the present invention.

Emulsion compositions of this invention wherein the aqueous phase comprises water and/or ethanol are particularly useful. In common with oil-in-water emulsions, water-in-oil emulsions are desirable from an economic, safety and environmental viewpoint as a means of preparing, storing, shipping and using efficacious components. In addition, emulsion compositions of aqueous or ethanol solutions have value as personal care compositions.

The base oil or volatile liquid continuous phase (b) is generally a fluid selected from the organosiloxane fluids having a normal, i.e. atmospheric pressure, boiling point of less than 2500° C. The volatile organosiloxane fluids have the average unit formula:

$$R_aSiO_{(4-a/2)}$$

wherein R is hydrogen or a substituted or unsubstituted hydrocarbon radical of from 1 to about 12 carbon atoms and "a" has an average value of from 2 to 3. Preferably, R is methyl and the organosiloxane is selected from the group consisting of $(CH_3)_3SiO_{1/2}$, $(CH_3)_2SiO_{2/2}$, $CH_3SiO_{3/2}$ and $SiO_{4/2}$ units. Preferably, the volatile methylsiloxane fluid consists essentially of dimethylsiloxane units, and optionally, trimethylsiloxane units. Of particular value as volatile liquid (b) are the cyclic siloxanes of the general formula $((CH_3)_2SiO)_b$ and the linear siloxanes of the general formula $(CH_3)_3SiO((CH_3)_2SiO)_cSi(CH_3)_3$, and their mixtures, wherein b is an integer of from 3 to 6 and c is an integer of from 0 to 4. A highly preferred methylsiloxane fluid is a mixture of the cyclic siloxanes wherein a major portion is tetramer, i.e. b=4.

Component (c) are organic oil-in-water type surfactants. These can be any cationic, anionic or nonionic organic surfactant suitable for preparing emulsions of the oil-in-water type and having a hydrophilic-lipophilic balance, HLB, value of from 8 to 18, inclusive. Examples of oil-in-water type surfactants include polyethoxylated quaternary ammonium salts and polyoxyethylene fatty amines as cationic surfactants, and polyethylene-glycol alkylethers, polyethylene-glycol alkylarylethers, polyethoxylated sorbitan monolaurate, polyethoxylated sorbitan monooleate, polyoxyethylene lanolin derivatives, and polyethoxylated fatty alcohols as nonionic surfactants. Mixtures of cationic and/or nonionic oil-in-water surfactants are also suitable. Other examples of suitable organic surfactants having an HLB value of from 8 to 18 may be found by consulting standard publications such as McCutcheon's "Detergents and Emulsifiers," 1975 North America Edition, MC Publishing Co., Glen Rock, N.J., 1975.

Component (d) comprises polyorganosiloxane polyoxyalkylene copolymer surface active agents. The copolymer surface active agents useful in the practice of the present invention are of the general formula:

$$MD_xD'_yM$$

wherein M, D, D', x and y are as previously defined.

The polysiloxane surface active agent may be prepared by well known methods. The preferred method is to introduce an alpha-beta unsaturated alcohol or carboxylic acid into the polymerization of alkylene glycols to produce a terminally unsaturated polyalkylene oxide. These terminally unsaturated polyalkylene glycols are subsequently added to silicon bonded hydrogens on suitable polysiloxanes. The addition reaction proceeds best in the presence of an active metal catalyst such as platinum.

The manufacture of the polysiloxane surface active agents is well known and understood by those skilled in the art. Methods of preparation are taught in U.S. Pat. Nos. 4,265,878; Re 25,727; 3,174,987; 4,122,029, and 3,172,899, all of which are hereby incorporated by reference.

The compositions of the present invention are generally prepared by first forming the aqueous phase A by mixing together components (a) and (c). Then the oily phase B is prepared by mixing together components (b) and (d). The additive (e) is then added to either phase A or B, depending upon the type of additive as known to those skilled in the art. The two phases are then mixed, preferably with high sheer agitation, to form an emulsion. Optionally, the emulsions may be further homogenized.

The lotions of the present invention can then be used in a wide variety of end products depending upon the additives employed. Typically, the lotions may be formulated into skin care creams, suntan lotions, make-up, facial scrubs and cleansing creams.

Preferred formulations are sunscreen lotions and personal care lotions. These may be formulated using the water-in-oil emulsions of the present invention. Such compositions contain (A) from about 89.5 to about 40 parts by weight water (B) from about 10 to about 45 parts by weight organosiloxane fluid, (C) from about 0.1 to about 3 parts by weight of an organic oil-in-water surfactant having an HLB value of 8 to 18, (D) from about 0.4 to about 20 parts by weight of polysiloxane surface active agent and (E) an effective amount of sunscreen or other desired skin care agent.

DESCRIPTION OF THE PREFERRED EMBODIMENTS

The following examples illustrate the present invention. They are not to be construed to limit the claims in any manner whatsoever.

EXAMPLES 1-3

A series of general skin care water-in-oil formulations were prepared using SF1228 combined with "POLYSORBATE 80" as the emulsifier system.

The emulsions are prepared according to the following: Part A, the oil phase, is prepared by mixing together 10 parts by weight SF-1228, a polyorganosiloxane polyoxyalkylene copolymer emulsifier, 6 parts by weight of SF-1202, a cyclomethylsiloxane fluid, and 4 parts by weight of isopropyl myristate, a liquid ester emollient. Part B, the aqueous phase, is prepared by mixing together 0.2 parts by weight of polysorbate 80, an organic oil-in-water surfactant, 3.0 parts by weight of propylene glycol, 1 part by weight of sodium chloride and 75.8 parts by weight of water.

Part B is then added to Part A with high shear agitation in a vessel, at room temperature. The emulsion formed is then milled in a Gifford-Wood homogenizer to increase stability.

Examples 2 and 3 are prepared according to the above procedure, varying the type of skin care additives. The compositional data is set forth below in Table 1.

TABLE 1

| SKIN CARE FORMULATIONS | | | |
|---|---|---|---|
| Examples | 1 | 2 | 3 |
| Part A, pbw | | | |
| SF-1228[a] | 10.0 | 10.0 | 10.0 |
| SF-1202[b] | 6.0 | 5.0 | 7.0 |
| Isopropl Myristate | 4.0 | 4.0 | — |
| Lanolin[c] | — | 1.5 | 1.0 |
| SS-4267[d] | — | — | 3.0 |
| Part B, pbw | | | |
| Polysorbate 80[e] | 0.2 | 0.2 | 0.2 |
| Glycerine | — | 3.0 | 3.0 |
| Propylene glycol | 3.0 | — | — |
| Sodium Chloride | 1.0 | 1.0 | 1.0 |
| Water | 75.8 | 75.3 | 74.8 |

[a] = Polyorganosiloxane Polyoxyalkylene copolymer, General Electric Company
[b] = Cyclomethylsiloxane Fluid, General Electric Company
[c] = Fluilan brand of lanolin made by Croda, Inc.
[d] = Methylsiloxane Fluid and Methylsiloxane resin
[e] = Ethoxylated sorbitan oleate All formulations passed 60 days at 40° C. stability testing and 4 freeze/thaw cycles at −10° C. for 8 hours and 25° C. for 16 hours.

EXAMPLES 4–5

The procedure of Example 1 is followed, except that various sunscreen additives are employed in the oil phase. For comparative purposes, two formulations similar to Example 4 are also prepared and tested back to back. In Example A, no polysorbate 80 is added; ad in Example B, polysorbate oleate (HLB 4.3) is employed in place of polysorbate 80 (HLB 15.0). The composition data is set forth below in Table 2.

TABLE 2

| SUN PROTECTION FORMULATIONS | | | | |
|---|---|---|---|---|
| Example | 4A* | 4B* | 4 | 5 |
| Part A, pbw | | | | |
| SF-1228[a] | 10.0 | 10.0 | 10.0 | 100 |
| SF-1202[b] | 12.0 | 12.0 | 12.0 | 100 |
| Octyl salicylate | — | — | — | 30 |
| Lonzest 143-S[c] | — | — | — | 30 |
| Lanolin[d] | 0.5 | 0.5 | 0.5 | — |
| Neoheliopan AV[e] | 5.0 | 5.0 | 5.0 | 60 |
| Micronized Titanium Dioxide | 3.0 | 3.0 | 3.0 | 30 |
| SS-4267[f] | 3.0 | 3.0 | 3.0 | — |
| Mineral Oil (70 SUS[g]) | 1.0 | 1.0 | 1.0 | — |
| Sorbitan Oleate | — | 0.2 | — | — |
| Part B, pbw | | | | |
| Polysorbate 80 | — | — | 0.2 | 02 |
| Glycerine | 3.0 | 3.0 | 3.0 | 30 |
| Sodium Chloride | 1.0 | 1.0 | 1.0 | 10 |
| Water | 61.5 | 61.3 | 61.3 | 608 |

\* = Comparative Example
[a] = Polyorganosiloxane polyoxyalkylene copolymer, General Electric Company
[b] = Cyclomethylsiloxane fluid, General Electric Company
[c] = Lonza, Inc. brand of myristal proprionate
[d] = Croda, Inc. brand of lanolin
[e] = Haarmann and Reimer Corp. brand of octylmethoxycinnamate
[f] = Methylsiloxane Fluid and Methyl Siloxane Resin
[g] = SUS is Saybolt Universal Seconds viscosity measurement The formulations within the scope of the appended claims (Examples 4 and 5) showed excellent stability (no separation) during a stability test at 40° C. for 60 days and also in testing at 4 freeze/thaw cycles. The formulations without the polysorbate 80 (Examples 4A* and 4B*) and unexpectedly lower viscosity than that of Example 4. Further, after 24 hours at 40° C., separation was noticeable in both Examples 4A* and 4B*, with Example 4B* being slightly worse than 4A*.

The above-mentioned patents are hereby incorporated by reference.

Many variations of the present invention will suggest themselves to those skilled in the art in light of the above-detailed description. All such obvious modifications are within the full intended scope of the appended claims.

We claim:

1. A lotion comprising:
   (a) from about 89.5 to about 40 parts by weight of an aqueous solution as a discontinuous phase;
   (b) from about 10 to about 45 parts by weight of a volatile liquid having a normal boiling point of less than 250° C. as a continuous phase, said volatile liquid being selected from the group consisting of organosiloxane fluids having the average unit formula $$(CH_3)_a SiO_{(4-a)/2} \qquad (I)$$

(c) from about 0.1 to about 3 parts by weight of an organic oil-in-water surfactant having an HLB value of from 8 to 18 inclusive; and
   (d) from about 0.4 to about 20 parts by weight of a polyorganosiloxane polyoxyalkylene copolymer surface active agent of the formula $$MD_x D'_y M \qquad (II)$$

wherein
   D is $R_2SiO_{2/2}$ where R is hydrogen or methyl, ethyl, vinyl, phenyl, trifluoropropyl or unsubstituted hydrocarbon radical of from 1 to about 12 carbon atoms;
   D' is $RR'SiO_{2/2}$ where R' is a polyalkylene ether of the formula $$-R^3{}_a-(OR^2)_n-OR^4 \qquad (III)$$

where $R^2$ is a $-CH_2-CH_2-$ group, $R^3$ is unsubstituted alkylene group of 1 to 20 atoms, $R^4$ is the same as R, n has a value of from 5 to about 20, and a is 0 or 1;
   M is trimethylsiloxy endcapping units;
   x is from about 335 to about 475; and
   y is from about 4 to about 23;
   with the proviso that the molecular weight of polysiloxane units D is from about 25,000 to about 35,000 and the weight ratio of D to D' is from greater than 60/40 to 90/10.

2. The lotion of claim 1 wherein the lotion showed no separation for 60 days at 40° C.

3. The lotion of claim 2 wherein the lotion showed no separation after 4 freeze/thaw cycles.

4. A lotion as defined in claim 1 which further comprises (e) a sunscreen agent.

5. A lotion as defined in claim 1, wherein said sunscreen agent is employed in the oil phase of the emulsion.

6. A lotion as defined in claim 5, wherein said sunscreen additive is selected from the group consisting of titanium dioxide, UVA sunblocks, UVB sunblocks and mixtures of any of the foregoing.

* * * * *